United States Patent [19]

Grollier et al.

[11] Patent Number: 4,495,203

[45] Date of Patent: Jan. 22, 1985

[54] ANHYDROUS COMPOSITION, STABLE TO OXIDATION, BASED ON ANTHRALIN OR ONE OF ITS DERIVATIVES, IN A CARRIER CONSISTING OF A FATTY ACID ALKYL ESTER AND A THICKENER, AND ITS USE IN THE TREATMENT OF SKIN DISEASES

[75] Inventors: Jean-Francois Grollier, Paris; Georges Rosenbaum, Asnìeres; Josiane Allec, Pierrefitte; Braham Shroot, Antibès, all of France

[73] Assignee: Societe Anonyme dite: L'OREAL, Paris, France

[21] Appl. No.: 435,983

[22] Filed: Oct. 22, 1982

[30] Foreign Application Priority Data

Oct. 23, 1981 [FR] France .................. 81 19952
Apr. 5, 1982 [FR] France .................. 82 05864

[51] Int. Cl.³ ............................................ A61K 31/05
[52] U.S. Cl. ...................................... 514/732; 424/365; 514/863
[58] Field of Search ........................ 424/346, 365

[56] References Cited

U.S. PATENT DOCUMENTS 4,203,969 5/1980 Yarrow et al. .................. 424/83
4,287,214 9/1981 Van Scott et al. .................. 424/346
4,299,826 11/1981 Luedders .................. 424/181
4,316,902 2/1982 Yu et al. .................. 424/266
4,367,224 1/1983 Van Scott et al. .................. 424/175

OTHER PUBLICATIONS

Remington's Pharmaceutical Sciences, 16th Ed., 1980, p. 356.
Chemical Abstracts 76:144782y (1972).
Cosmetics, Science & Technology (Balsam et al.), 2nd Ed., vol. 1, pp. 194–195, (1972).

*Primary Examiner*—Leonard Schenkman
*Attorney, Agent, or Firm*—Wegner & Bretschneider

[57] ABSTRACT

Anhydrous composition, stable to oxidation, of anthralin or a derivative thereof.

This composition contains anthralin or a derivative thereof in a carrier composed of (i) at least one fatty acid alkyl ester, the fatty acid having 12 to 18 carbon atoms and the alkyl radical having 2 or 3 carbon atoms, and (ii) at least one thickener taken from the group made up of silicas having particle sizes less than 30 m$\mu$ and polyethylene powders having densities between 0.9 and 0.96 (g/cm³).

This composition is used in the treatment of skin diseases, particularly psoriasis.

6 Claims, No Drawings

ANHYDROUS COMPOSITION, STABLE TO OXIDATION, BASED ON ANTHRALIN OR ONE OF ITS DERIVATIVES, IN A CARRIER CONSISTING OF A FATTY ACID ALKYL ESTER AND A THICKENER, AND ITS USE IN THE TREATMENT OF SKIN DISEASES

The present invention relates to an anhydrous composition, which is stable to oxidation, based on anthralin or one of its derivatives, and to its use for the treatment of skin diseases and in particular for the treatment of acne, warts, and especially psoriasis.

Psoriasis is a particularly frequent form of dermatosis which manifests itself as lesions found on the elbows, on the back of the forearms, on the knees, on the legs and in the sacro-lumbar regions, as well as on the scalp.

Amongst the various substances which have already been recommended for the treatment of psoriasis, special mention must be made of anthralin or dithranol (1,8,9-trihydroxyanthracene), which has proved particularly active, but the use of which is not without certain disadvantages insofar as this compound is very readily degraded by oxidation to give dark-coloured polymeric products capable of staining the skin and clothes.

In order to prevent its degradation, it has been proposed to use it in association with certain stabilizers or antioxidants in thickened vehicles, in particular in vaseline, for the purpose not only of improving stability but also of providing compositions which can be applied to the skin to be treated without flowing onto the healthy parts of the skin, and thus to prevent the irritation phenomena encountered with fluid compositions.

Despite the presence of stabilizers or antioxidants, such as butylhydroxytoluene (BHT), butylhydroxyanisole (BHA) or, alternatively, certain α-hydroxyacids, it has not been possible to obtain thickened compositions having good stability for a long time, in particular because of the thickeners employed.

It has now been found, according to the present invention, that it is possible to obtain compositions having an excellent consistency and having very good stability with time at ambient temperature, without it being necessary to use stabilizers or antioxidants, by incorporating anthralin or one of its derivatives into a carrier consisting of certain higher fatty acid esters mixed with certain silicas or polyethylene powders.

The invention is therefore based not only on the choice of particular fatty acid alkyl esters but also on the choice of thickeners.

Experiments on preservation have in fact made it possible to show that only silicas and polyethylene powders are capable of providing stable compositions, the coloration of the compositions remaining constant or essentially constant; physicochemical determinations confirm this good stability. This was not the case with other thickeners, such as certain modified clays, such as bentones, or certain alumino-silicates, such as zeolites.

The present invention has as an object, as a new industrial product, an anhydrous composition, which is stable to oxidation, based on anthralin or one of its derivatives, for the treatment of skin diseases, in particular psoriasis, this composition containing anthralin or one of its derivatives in a carrier consisting of (i) at least one fatty acid alkyl ester, the fatty acid having from 12 to 18 carbon atoms and the alkyl radical, which is branched or unbranched, having 2 or 3 carbon atoms, and (ii) at least one thickener taken from the group comprising silicas having a particle size of less than 30 mµ and polyethylene powders having a density of between 0.9 and 0.96 (g/cm$^3$).

Amongst the alkyl esters corresponding to the above definition, there may be mentioned isopropyl laurate, isopropyl myristate, isopropyl palmitate, ethyl myristate and mixtures thereof.

Amongst the anthralin derivatives which can be used, there may be mentioned the compounds described in French Patent Applications Nos. 80/22,454 and 80/22,455.

According to the invention, the concentration of anthralin or of one of its derivatives in the composition is generally from 0.01 to 5%, and preferably 0.1 to 3%, the concentration of the fatty acid alkyl ester is generally from 60 to 99% and the concentration of the silica and/or the polyethylene powder is generally from 0.1 to 20% by weight, and preferably 2 to 15% by weight, relative to the total weight of the composition.

Amongst the silicas having an average particle diameter of less than 30 mµ, there may be mentioned those sold under the names "Aerosil 200" and "Aerosil R 972" by Degussa and those sold under the name "HDK," in particular the silica "HDK N 20 E," by Wacker, these silicas being used by themselves or in a mixture.

Amongst the polyethylene powders as defined above, which can be used according to the invention, there may be mentioned:

(1) The polyethylene powders of the low-density type having a melting point of 104°–113° C., determined by the ASTM method D 2117-64, and a density at 23° C. of 0.914 to 0.923 (g/cm$^3$), determined by the ASTM method D 2839. As examples of polyethylene powders possessing these characteristics, there may be mentioned those sold under the names "Lotrene UA 7000 S" and "Lotrene UA 4000 S" by C. D. F. Chimie.

(2) The polyethylene powders of the high-density type having a softening point of 128°–129° C., determined by the ASTM method E 28, and a density of 0.96 (g/cm$^3$), determined by the ASTM method D 1505. As examples of polyethylene powders possessing these characteristics, there may be mentioned those sold under the names "Polymist B6" and "Polymist B12" by Allied Chemical.

(3) The polyethylene powders having a softening point of 102°–117° C., determined by the ASTM method E 28, and a density of 0.90 to 0.94 (g/cm$^3$), determined by the ASTM method D 1505. As an example of a polyethylene powder possessing these characteristics, there may be mentioned that sold under the name "Polyethylene AC 6A" by Allied Chemical, and (4) The ethylene/acrylic acid copolymers having a softening point of 92°–108° C., determined by the ASTM method E 28, and a density of 0.93 (g/cm$^3$), determined by the ASTM method D 1505. As an example of a powder possessing these characteristics, there may be mentioned that sold under the name "Polyethylene AC 540" by Allied Chemical.

The compositions according to the invention can also contain various conventional ingredients, such as salicylic acid.

Several non-limiting examples of compositions according to the invention based on anthralin or one of its derivatives will now be given for purposes of illustration.

EXAMPLE 1

A gel for the skin is prepared according to the invention by mixing the following ingredients:

| | |
|---|---|
| Anthralin | 0.4 g |
| Silica "HDKN 20 E" | 7.0 g |
| (pyrogenic silica sold by WACKER) | |
| Isopropyl myristate q.s | 100 g |

EXAMPLE 2

A gel for the skin is prepared according to the invention by mixing the following ingredients:

| | |
|---|---|
| Anthralin | 3 g |
| Silica "Aerosil R972" | 8 g |
| Salicylic acid | 0.2 g |
| Isopropyl myristate q.s. | 100 g |

EXAMPLE 3

A gel for the skin is prepared according to the invention by mixing the following ingredients:

| | |
|---|---|
| Anthralin | 5 g |
| Silica "Aerosil 200" | 8 g |
| Isopropyl myristate q.s. | 100 g |

In this example, the silica "Aerosil 200" can be replaced by the same amount of the silica "HDK N 20 E."

EXAMPLE 4

A gel for the skin, for the treatment of psoriasis, is prepared according to the invention by mixing the following ingredients:

| | |
|---|---|
| Anthralin | 1 g |
| Polyethylene powder AC 6A | 7.5 g |
| Isopropyl myristate q.s. | 100 g |

In Examples 1 to 4 above, the isopropyl myristate can be replaced by an equivalent amount of isopropyl palmitate, isopropyl laurate or ethyl myristate.

EXAMPLE 5

A gel for the skin, for the treatment of psoriasis, is prepared according to the invention by mixing the following ingredients:

| | |
|---|---|
| Anthralin | 1 g |
| Polyethylene powder AC 540 | 7.5 g |
| Ethyl myristate q.s. | 100 g |

In this example, the ethyl myristate can be replaced by the same amount of isopropyl myristate.

When applied to the parts of the skin or scalp to be treated, in an amount sufficient to cover the lesions, compositions 1 to 5 above make it possible, after a treatment period of about 3 to 5 weeks, to effect a regression and cure of the skin diseases, in particular psoriasis.

We claim:

1. A stable to oxidation, anhydrous composition for treatment of diseases of the skin and particularly for psoriasis, containing 0.01 to 5% by weight of anthralin in a carrier comprising 60 to 99% by weight of a fatty acid alkyl ester, the fatty acid having from 12 to 18 carbon atoms and the alkyl radical having 2 to 3 carbon atoms, and 0.1 to 20% by weight of a thickener selected from the group consisting of silica having an average particle diameter of less than 30 m$\mu$ and ethylene polymer powder having a density of 0.9 to 0.96 (g/cm$^3$).

2. The composition of claim 1 wherein the fatty acid alkyl ester is selected from the group consisting of isopropyl laurate, isopropyl myristate, isopropyl palmitate, ethyl myristate and mixtures thereof.

3. The composition of claim 1 wherein anthralin is present at a concentration of 0.1 to 3% by weight.

4. The composition of claim 1 wherein the concentration of silica and/or polyethylene powder is from 2 to 15% by weight.

5. The composition of claim 1 which also contains salicyclic acid.

6. A process for the treatment of skin diseases, particularly for psoriasis, comprising applying to the skin lesions to be treated an effective amount of the compositions of claim 1.

* * * * *